United States Patent [19]

Schmitt

[11] 4,442,042

[45] Apr. 10, 1984

[54] PROCESS OF MAKING PROPANE SULFONATES

[75] Inventor: Kirk D. Schmitt, Pennington, N.J.

[73] Assignee: Mobil Oil Corporation, New York, N.Y.

[21] Appl. No.: 259,218

[22] Filed: Apr. 30, 1981

[51] Int. Cl.³ ................. C07C 143/11; C07C 143/06; C07C 143/38
[52] U.S. Cl. ........................... 260/512 R; 260/505 R; 260/512 C; 568/38; 568/45; 568/59; 568/608; 568/673; 568/689
[58] Field of Search ........... 260/513 B, 512 R, 512 C, 260/505 R; 568/689, 608, 673, 38, 45, 59

[56] References Cited

U.S. PATENT DOCUMENTS

| | | | |
|---|---|---|---|
| 4,091,014 | 5/1978 | Johnson, Jr. et al. | 260/512 R |
| 4,222,957 | 9/1980 | Watts et al. | 260/512 R |
| 4,226,807 | 10/1980 | McCoy | 260/512 R |
| 4,267,123 | 5/1981 | Chen et al. | 260/501.12 |

OTHER PUBLICATIONS

Freedman et al., Tet. Lett., 1975, pp. 3251–3254.

*Primary Examiner*—Nicky Chan
*Attorney, Agent, or Firm*—Charles A. Huggett; Michael G. Gilman; Edward J. Trojnar

[57] ABSTRACT

An improved process for making propane sulfonates without isolating intermediates is provided comprising using an aqueous NaOH system instead of metallic sodium and recycling a portion of the product phase transfer as catalyst.

8 Claims, 1 Drawing Figure

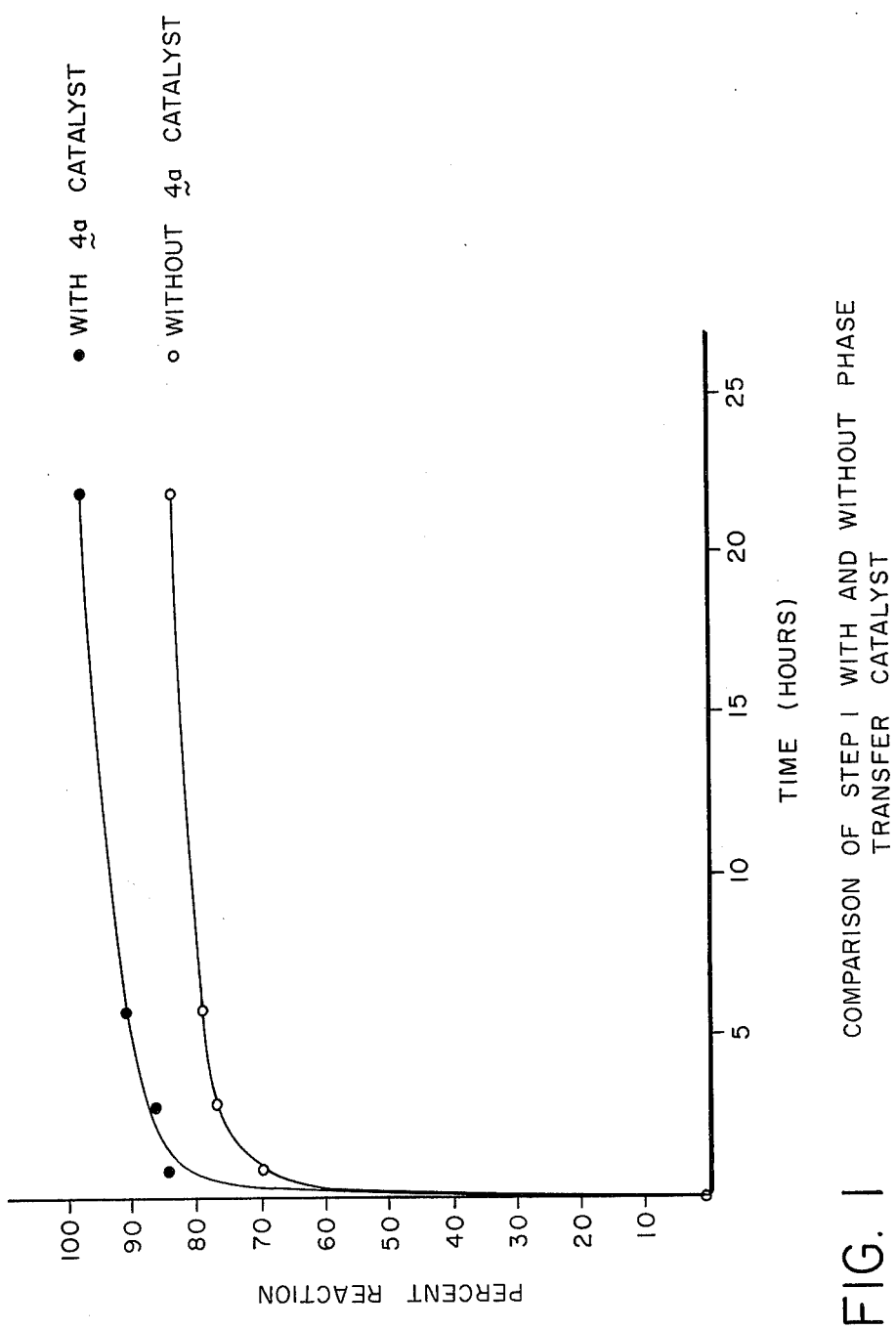

PROCESS OF MAKING PROPANE SULFONATES

This application is related to pending application Ser. No. 96,947 filed Nov. 23, 1979 and entitled Method of Making Propane Sulfonates, now U.S. Pat. No. 4,267,123.

BACKGROUND OF THE INVENTION

1. Field of the Invention

This application is directed to an improved process of making propane sulfonates which are useful as surfactants having high tolerance for brine and excellent thermal and hydrolytic stability.

2. Description of the Prior Art

Propane sulfonates of various polyethoxylated alcohols are known surfactants. Propane sulfonates are also known to have high tolerance for brine coupled with thermal and hydrolytic stability. However, propane sulfonates of alcohols and thiols have only been prepared in the literature by reaction of alkali metal salts of the alcohols or thiols with propane sulfone. This is a convenient high yield laboratory synthesis but is not desirable on a large scale for several reasons. Foremost among them are the fact that (1) such a reaction requires multistep synthesis and purification of propane sultone (2) propane sultone is expensive to purify and its overall yield of 80–90% limits the yield in the preparation of propane sulfonates and (3) propane sultone is a known carcinogen. Therefore processes involving the use of propane sultone must utilize expensive controls to minimize worker exposure but despite such controls its use will always engender some risk.

The preparation of allyl ethers or sulfides is also well known in the literature, however, the use of the procedure described herein to convert alcohols or thiols to propane sulfonates in a single reactor as far as is known to applicant is novel and unobvious. There is, however, one report in the literature of a two step attempt at a similar process for the preparation of propane sulfonates of tertiary amines [*J. Amer. Oil Chem. Soc.,* 53, 60 (1976)] but it reports the process produces excessive quantities of undesirable "iso-sulfonate" whose presence degrades the performance of the product. This of course is most undesirable.

SUMMARY OF THE INVENTION

This invention is more particularly directed to a process for making propane sulfonates from alcohols in an aqueous system without isolating intermediates by (1) using 50% NaOH instead of metallic sodium as previously used, and (2) recycling a portion of the product surfactant as a phase transfer catalyst to ensure intimate contact of the reactants. This synthesis is far more efficient than any prior art methods known to applicants.

In accordance with the below described reactions propane sulfonates 4 where R is such that the solubility of compound 3 in water is less than 0.5% can be prepared in two steps in a single reactor without isolation of intermediates in almost 100% yield by control of the reaction conditions in steps (1) and (2).

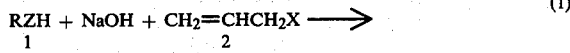

RZCH$_2$CH=CH$_2$ + NaX (3)

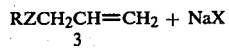

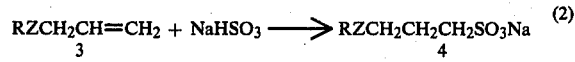

The reaction of step (1) is usually conveniently carried out in an organic solvent with metallic sodium (instead of NaOH) in two separate steps. The organic solvent and any excess allyl halide, 2, must then be distilled and dried before reacting in another reactor.

It has now been discovered that the reaction of step (1) where R is C$_1$–C$_{16}$ alkyl, alkaryl, alkylpolyoxyethylene, or alkaryl-polyoxyethylene, X is halide or tosylate and Z or O or S, may be carried out in a completely aqueous system if 50% NaOH is used as the base and if close contact between the water insoluble allyl halide and alcohol is brought about by inclusion of a certain minimum amount of desired final product 4 in the reaction vessel. At the end of the reaction any excess allyl chloride is easily distilled from the reactor. It need not be dried but may be recycled directly nor must it be separated from an organic solvent since none is used.

The preparation of allyl ethers by the reaction of sodium or sodium methoxide with the alcohol followed by reaction with allyl chloride all in an organic solvent such as toluene or tetrahydrofuran (the Williamson ether synthesis) is well known and may be found in many standard textbooks on organic chemistry.

The reaction of allyl chlorides and alcohols with NaOH is less well known but does occur if correct phase transfer catalysts are added. Such catalysts are invariably salts of the tetraalkyl ammonium ion. Thus H. H. Freedman in *tetrahedron Letters* 3251 (1975) reports that the reaction of allyl alcohol with benzyl chloride may be achieved with NaOH as base if benzyl triethylammonium chloride is used as a phase transfer catalyst. The yield is only 72%. If such a tetraalkylammonium chloride is used, it would have to be separated from our product and recycled in order that it not contaminate the product or represent a loss of expensive material. Such a process would be expensive.

Propane sulfonates of alcohols have only been prepared in the literature by reaction of alkali metal salts of the alcohols with propane sultone, reaction (3). This is a convenient high yield laboratory synthesis but is not desirable on a large scale for reasons discussed hereinabove.

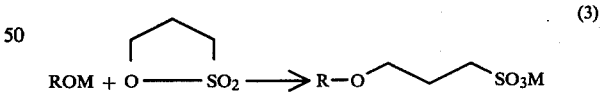

The reaction of NaHSO$_3$ with simple olefins has been much studied. The literature teaches that for simple water-soluble olefins or olefins which can be made soluble by the addition of small amounts of alcohols all that is required for high conversions to the desired products are conditions in which all reagents are dissolved in a single phase.

The present invention is based substantially on the discovery that allyl ethers do not behave this way. Conditions may be found in which all the reagents are dissolved in a single phase in alcohol and water and yet conversion will not exceed 40 or 50% unless a minimum amount of sulfonate is added. When such minor amount of propane sulfonate is added to the reaction medium the conversion is rarely below 90%.

The early literature on the reaction of NaHSO3 with olefins indicated that S-alkylation leading to sulfonate products might be accompanied by a slight amount of O-alkylation leading to sulfites but even this slight formation was disputed and the literature for the last thirty years reveals that sulfites are actually not by-products of the sulfitation of olefins. It is therefore quite surprising that sulfitation of allyl-ethers can produce as much as 100% sulfite in solvents which are taught in the literature to be acceptable for sulfitation of ordinary olefins to sulfonates. A high yield of sulfite would also be surprisingly because the literature teaches that solvent systems which produce high conversions of olefins will produce high yields of sulfonates.

BRIEF DESCRIPTION OF THE DRAWING

The drawing is a comparison of step 1 in accordance with the invention with and without recycled product as a phase transfer catalyst or agent.

DESCRIPTION OF PREFERRED EMBODIMENTS

The following examples illustrate the conditions necessary for high conversion and high yield in both steps (1) and (2) in a single reactor. General reaction conditions are: temperature 0°–55° C.; atmospheric pressure from about 1:1 to about 1:10 molar ratio of recycled product to allyl halide.

Examples (1) and (2) illustrate some specific conditions needed for step (2) previously described hereinabove.

Compound 3a (refer to equation 4 hereinbelow) was prepared using known methods from commercially available compound 1a via reaction 4. Authentic compound 4a was prepared from compound 1a via reaction 3 as disclosed hereinabove. The compounds were analyzed by high pressure liquid chromatography (HPLC) and carbon thirteen nuclear magnetic resonance (C-13 NMR) as described in Example 1.

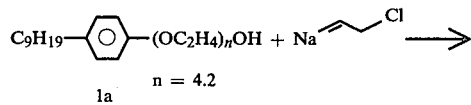

1a, n = 4.2

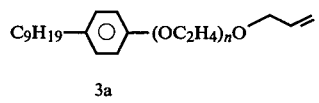

3a

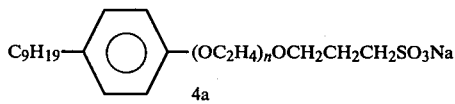

4a

Example 3 as disclosed hereinbelow illustrates the complete one reactor sequence of steps 1 and 2.

Example 4 shows the clear advantage of the use of recycled propane sulfonate as a phase transfer agent in step (1).

EXAMPLE 1

This example illustrates that high conversions of allyl ether may be achieved without high yields and describes the analytical procedures which establish the structure of the sulfite product.

A one-liter 4-neck flask equipped with a mechanical stirrer was charged with 120 ml methanol, 75 ml H2O, 27 g sulfonate (4a) and 66.9 g allyl ether (3a). A homogeneous solution resulted which was stirred at about 800–1000 RPM while air was passed through the flask at about 15 ml/min and a solution of 18.72 g NaHSO3 and 11.34 g Na2SO3 in 69 ml H2O was added dropwise over about one hour. Stirring was stopped occasionally and the reaction mixture analyzed by HPLC on a Water's Associates -μ-Bondpak C-18 column using 0.05 M Bu4N+H2PO4 in 86% methanol-14% H2O as eluant. A UV detector set for 277 nm was used. Since each of the compounds has the same UV chromophore with λmax=277 nm the output of the detector could be translated directly into mole percent. As the reaction proceeded the temperature rose exothermally about 5° C. Analysis by HPLC showed three materials with retention volumes 4.3 ml, 6.7 ml, and 34.4 ml. The second and third peaks had retention volumes identical to the sulfonate (4a) and the allyl ether (3a), respectively. Within two hours of the start of the reaction HPLC analysis indicated 95% of the allyl compound (3a) had reacted but only 15% of this had been converted to sulfonate (4a). The rest had been converted into sulfite (5a) (described below) whose structure was shown by C-13 NMR and chemical degradation.

The reaction was let stand overnight then filtered from precipitated inorganic salts, evaporated on a rotary evaporator and a C-13 NMR obtained. In addition to the peaks expected for sulfonate (4a) (by comparison to a spectrum of authentic 4a) two additional peaks due to one carbon each were seen at 62.9 ppm and 25.1 ppm. These are assigned to the NaO2—S—O—CH2—CH2— carbons of sulfite 5a.

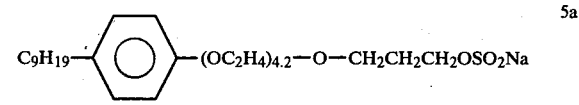

This material was shown to be the sulfite by heating the reaction product at 60° C. at 0.05 mm Hg for four hours. A gas was collected in a Dry Ice trap. Infrared analysis showed this gas to be sulfur dioxide. Carbon-13 NMR of the remaining material in moist CDCl3 shows the peak at 62.9 ppm to be gone and a new peak at 57.4 ppm to have appeared. This new chemical shift is identical to that of 3-methoxy-1-propanol. These results are summarized below by reaction (5).

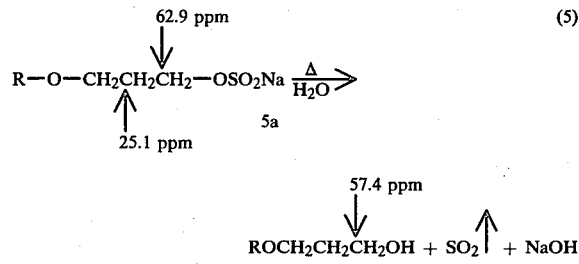

EXAMPLE 2

The same reaction as Example 1 was carried out with ethanol substituted for methanol to illustrate the critical control that the specific reaction conditions exercise over the course of sulfitation of allyl ethers. After three hours the conversion of 3a was 99% and the yield of sulfonate was not 14% as in Example 1 but 92%. Such a complete reversal of selectivity is completely unexpected and unobvious in view of prior art literature teachings.

EXAMPLE 3

Example 3 illustrates the complete process in one reactor. NOTE: The HPLC conditions used for Example 3 and 4 were different from those of Examples 1 and 2.

The samples were injected into a Whatman ODS C-18 column and eluted at 2 ml/min with a solvent whose composition changed linearly from 70% methanol (30% $H_2O$) to 100% methanol over 15 minutes. Under these conditions, compounds 4a and 5a had retention volumes of from 3.6 to 6.1 ml, compound 1a had a retention volume of 14.4 ml and compound 3a had a retention volume of 18.8 ml. Thus, to a 4 N 250 ml flask were added 19.3 g allyl chloride (0.252 mole), 10 g 51% NaOH (0.128 mole), 20.3 g 1a (0.050 mole) and 5.05 g 4a (0.0092 mole). The mixture was heated to reflux and stirred mechanically under argon. Aliquots were removed periodically and analyzed by HPLC. The results are shown in the Table.

TABLE

| Time at Reflux | % Reaction (Example 3) | % Reaction (Example 4) |
|---|---|---|
| 1 hr | 84% | 70% |
| 3 hr | 86 | 77 |
| 6 hr | 91 | 79 |
| 22 hr | 97 | 83 |

At the end of the reflux period the excess allyl chloride was distilled off, the reaction cooled, air flowed through the flask at about 15 ml/min and 40 ml 95% ethanol were added. After stirring briefly to assure air saturation a solution of 15.7 g $NaHSO_3$ and 3.6 $Na_2SO_3$ in 42 ml $H_2O$ was added dropwise over 15 min. An exotherm took the temperature to 34° C. and HPLC analysis after 3 hours indicated less than 1% allyl ether (3a) remained. An aliquot was stripped and analyzed by C-13 NMR as in Example 1. It showed 4% sulfite (5a) to be present so the overall conversion of 1a was $0.97 \times .99 = 96\%$ and the overall yield of propane sulfonate (4a) was $0.96 \times .96 = 92\%$.

The flask was cooled to 15° C., inorganics filtered off and the ethanol and water removed to give 33.5 g of pale yellow wax.

EXAMPLE 4

Example 4 shows the advantages of adding of minor amounts of the desired final product as phase transfer agent to step 1. It should be noted that although reaction does occur with compound 1a it is neither as fast nor as complete as when minor amounts of the desired final product are (4a) added to the reaction zone.

In this example 1a is a polyethyleneoxy alcohol. Such alcohols are known to act themselves as phase transfer agents (see for example, *Journal of Organic Chemistry,* 45, 1095 (1980). Thus, 1a (polyethyleneoxy) catalyzes its own reaction at the beginning of the reaction but as it is converted to allyl ether the reaction slows and stops (see FIGURE). If the alcohol were not a polyethyleneoxy alcohol but were a normal alcohol no reaction would occur as documented in the article by Freeman cited above.

19.3 Allyl chloride, 30.3 g alcohol, 1a, and 10 g 51% NaOH were stirred and refluxed under argon and the reaction analyzed by HPLC using the conditions of Example 3. The Table shows the progress of the reaction.

The FIGURE shows a comparison of the percent reaction with and without 1a added. Clearly addition of 1a gives faster and more complete reaction.

Our present procedure substitutes inexpensive sodium hydroxide for expensive metallic sodium, inexpensive wet conditions for expensive anhydrous, completely eliminates the use of and concommittantly recycle costs for organic solvent and allows one reactor to be used for the entire process with no sacrifice in yield or product quality.

I claim:

1. A method of preparing propane sulfonates from alcohols or thiols via their allyl ethers comprising conducting, under suitable conditions, a reaction in accordance with the following 2-step procedure in a single reactor without isolation of intermediates:

$$RZH + NaOH + CH_2=CHCH_2X \rightarrow RZCH_2CH=CH_2 + NaX \quad (1)$$

$$RZCH_2CH=CH_2 + NaHSO_3 \rightarrow RZCH_2CH_2CH_2SO_3Na \quad (2)$$

where R is $C_1$–$C_{16}$ alkyl, alkaryl, alkyl-polyoxyethylene or alkarylpolyoxyethylene, X is halide or tosylate, Z is O or S, and where the NaOH is an approximately 50% aqueous system; and recycling to (1) a minor amount of the desired product sufficient to function as phase transfer catalyst for said reaction, whereby the yield is improved compared to the reaction conducted in the absence of recycled product.

2. The method of claim 1 wherein X is chloride or bromide.

3. The method of claim 1 wherein R is alkaryl polyoxyethylene.

4. The method of claim 3 where R is

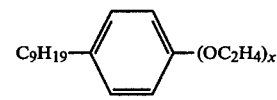

and x is 4.2.

5. The method of claim 1 in which Z is O.
6. The method of claim 1 in which Z is S.
7. The method of claim 1 or 6 in which the yield is substantially 100%.
8. The method of claim 1 in which excess $CH_2=CHCH_2X$ is distilled off.